US006731804B1

(12) United States Patent
Carrieri et al.

(10) Patent No.: US 6,731,804 B1
(45) Date of Patent: May 4, 2004

(54) THERMAL LUMINESCENCE LIQUID MONITORING SYSTEM AND METHOD

(75) Inventors: Arthur H. Carrieri, Abingdon, MD (US); Erik S. Roese, Baltimore, MD (US); Stephen J. Colclough, Baltimore, MD (US); Peter J. Schlitzkus, Baltimore, MD (US); V. Kenneth Younger, Bel Air, MD (US); James R. Orndoff, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 606 days.

(21) Appl. No.: 09/672,073

(22) Filed: Sep. 28, 2000

(51) Int. Cl.$^7$ ................................................. G06K 9/46
(52) U.S. Cl. ........................ 382/191; 382/128; 382/159
(58) Field of Search ............................... 382/128, 150, 382/159, 181, 190, 191; 250/253, 341.6; 374/5, 45

(56) References Cited

U.S. PATENT DOCUMENTS

| | | | | |
|---|---|---|---|---|
| 4,236,071 A | * | 11/1980 | Chimenti | 250/253 |
| 4,365,975 A | * | 12/1982 | Williams et al. | 48/197 R |
| 4,496,839 A | * | 1/1985 | Bernstein et al. | 250/341.6 |
| 5,164,597 A | * | 11/1992 | Lodder | 250/341.8 |
| 5,228,776 A | * | 7/1993 | Smith et al. | 374/5 |
| 5,241,179 A | * | 8/1993 | Carrieri | 250/341.6 |
| 5,368,171 A | * | 11/1994 | Jackson | 134/147 |
| 5,792,668 A | * | 8/1998 | Fuller et al. | 436/149 |
| 6,343,534 B1 | * | 2/2002 | Khanna et al. | 89/1.13 |
| 6,464,392 B1 | * | 10/2002 | Carrieri et al. | 374/45 |

* cited by examiner

Primary Examiner—Daniel Mariam
(74) Attorney, Agent, or Firm—Ulysses John Biffoni

(57) ABSTRACT

A Thermal Luminescence Water Monitor system and method for real-time remote sensing and identification of chemical and biological materials (CBMs) in a liquid source, comprising an irradiation component having a microwave radiation source tuned to water's vibration-rotation exciting energy, a glass cell for holding a liquid sample contained within a sealed chamber for its irradiation and concomitant liberation of thermal luminescence, a spectrometer analysis component for collecting and processing thermal luminescence emissions, a neural network component for filtering thermal luminescence difference-spectra components and pattern recognition of predetermined CBMs to determine their presence in the liquid source.

21 Claims, 8 Drawing Sheets

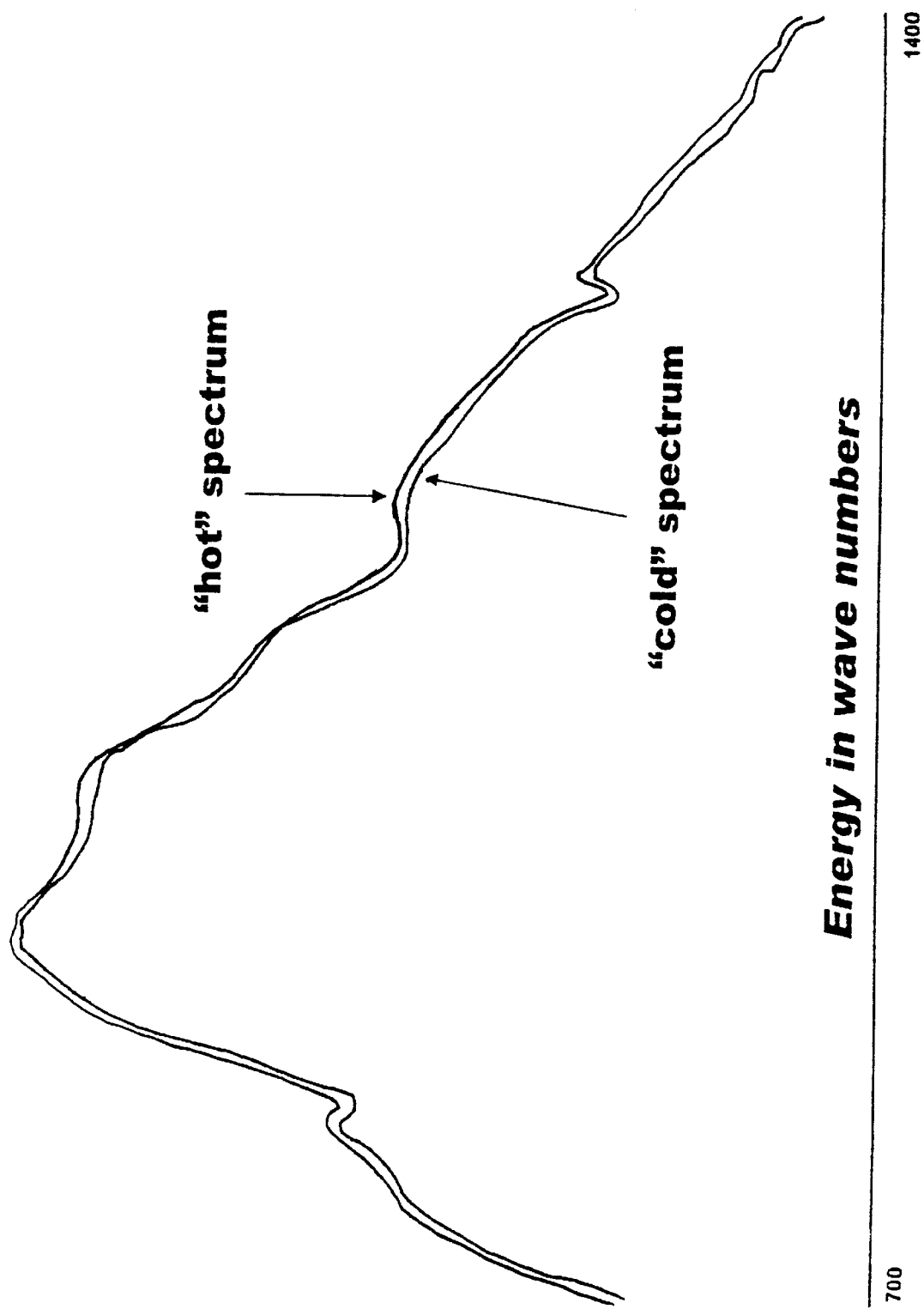

THERMAL LUMINESCENCE LIQUID MONITORING SYSTEM AND METHOD

GOVERNMENT INTEREST

The invention described herein may be manufactured, licensed, and used by or for the U.S. Government.

FIELD OF THE INVENTION

The invention concerns a remote sensing system and method for identification of chemical and biological materials dissolved in liquids that uses microwave radiation to stimulate thermal luminescence of contaminants to develop a fingerprint absorption profile of these contaminants.

BACKGROUND OF THE INVENTION

This invention relates to a system for remotely sensing and identifying contaminants in liquids, by using microwave irradiation to stimulate thermal luminescence of contaminants and a combination of spectroscopy and neural network technologies to classify their fingerprint spectra.

Liquid quality analysis systems and methods for identification of contaminants are well known. For example, detection and classification of chemical impurities in a water source are required by most municipal, industrial, and military operations. Accurate real-time detection and classification of hazardous pollutants in waste water discharges and water supplies are necessary for timely mitigation of hazards by any combination of process modification, purification, or rejection of its use or consumption, e.g., when the presence of a particular contaminant is known, specific remedial measures may then be implemented.

One technique for measuring volatile substances in liquids is the "purge and trap" method. In this technique organics are captured by passing the output of a sparging (bubbling) of an inert gas through a sample volume of the liquid being tested through a trap. This can be a lengthy process, especially if a gas chromatograph is used to measure the various concentrations of contaminants. Gas chromatography is also a maintenance-intensive technique. Doyle, et al, U.S. Pat. No. 5,421,194, describe a sparging-infrared (IR) liquid analyzing system which overcomes these drawbacks but still requires that a mechanism be provided for an inert gas to be bubbled through a sample volume of the liquid being analyzed and a condenser be provided between the sparging vessel and the IR gas cell to reduce water vapor interference with measurements. Their approach is complex.

Another sparging technique, developed by the Du Pont Corporation, sprays a water sample through a volume of inert gas. This approach requires collecting and recirculating the sprayed sample through the spraying process step until all the gas is saturated and consequently implementations of the technique perform in less than real-time. Further, this technique does not address the overlap of water vapor absorption bands with contaminant absorption bands and therefore cannot be used to detect many solutes, although it met Du Pont's needs.

Such liquid quality analysis systems and devices are not completely satisfactory and, in practice, are complex to operate and maintain, do not provide remote, real-time contamination identification, and can be inapplicable to a large number of possible solutes.

The present Applicants have devised, embodied, and tested this invention to overcome these shortcomings of the state of the art and to obtain further advantages.

SUMMARY OF THE INVENTION

The present invention achieves a system and method that provide ongoing remote sampling and analysis of liquid quality in real-time, directly from the liquid source and that accurately identifies chemical and biological materials (CBMs) dissolved in the liquid.

In addition, the present invention achieves a system and method that are accurate and reliable for specific expected contaminants.

The present invention provides a real-time pseudo-active remote sensing system and associated method that learn the features of expected contaminants of liquid sources to be monitored by using a neural network that incorporates the features of these specific anticipated contaminants in advance of monitoring activities. The neural network is then used to match the features of detected contaminants with the features already learned.

In a particular embodiment, called a Thermal Luminescence Water Monitor or TLWM, a water-solute sample is drawn and held in a cell structure designed with an infrared transmission window. The cell structure is coupled to a magnetron or klystron source for generating an energetic microwave beam. Analysis to identify dissolved materials, such as chemical agents and other hazardous organic compounds, is accomplished using this cell structure and the method of the present invention, in which microwave light irradiates the liquid-solute sample along the length of the cylindrical glass cell through the cell wall. The water-solute media rises in temperature during this microwave irradiation, due to absorption of the microwave energy, while concomitantly emitting increasing levels of thermal luminescence through the cell's infrared window to a sensor. The TLWM and method are pseudo-active technology in that the external microwave radiation source that heats the water sample is itself required to be outside the bandwidth of the sensor's photosensitive detector element.

More particularly, when the liquid being monitored is water, the TLWM and method embodiment of the present invention irradiates the water-solute contained in the sample cell with microwave energy of about 2.45 GHz, with 2.45 GHz being preferred. This frequency is the intense water molecular vibration-rotation absorption line, which excites the water molecules into a strong vibration-rotation state. The microwave source can be operated in pulsed or continuous-wave modes. This coupling of microwave energy into the water molecule is partly converted into heat energy. The manifestation of thermal emissions emitted by the heated sample in the 700–1400 $cm^{-1}$ middle infrared region of the electromagnetic spectrumis the detection principal of the TLWM and method. This middle infrared region of emissions is the fingerprint region where most organic contaminants of interest possess unique spectra. It is also the detection bandwidth of the system and method of the present invention.

In an exemplary embodiment of the system and method of the present invention, a Fourier Transform-Infrared (FT-IR) spectrometer is employed as a sensor device which is positioned to intercept the thermal luminescence emitted from the glass cell and to direct the thermal luminescence flux to a Michelson interferometer as its scanning component. That is, the FT-IR spectrometer collects the concomitant broad middle infrared emissions given off by the irradiated sample and then focuses it onto a photoconductive chip where the radiant thermal luminescent light is converted to interferogram temporal voltage waveforms that represent summed constructive and destructive frequencies of the collected thermal luminescence light. The interferogram is subsequently transformed, by a fast Fourier Transform operation, into an infrared Graybody spectrum that resembles a Gaussian-like profile.

Contiguous sets of these Graybody spectra are grouped as the liquid-solute sample rises in temperature, due to absorption of the irradiating microwave beam. The adjacent spectra collected when the heating rate is maximum, i.e., when $$\frac{\partial^2 T}{\partial t^2} = 0$$

where

T=temperature of the sample t=microwave irradiation time are isolated, subtracted, and pre-processed by computer algorithms for submission to a neural network.

Pluralities of interferograms/spectra are acquired/pre-processed in this manner during a period of microwave irradiation. The system and method of the present invention thus measure a thermal luminescence difference-spectrum during an irradiation interval associated with a peak heating rate (or state of maximum thermal luminescence flux) and analyze the resulting spectral information to identify contaminants through their fingerprint absorption profiles. For this analysis, the system and method of one embodiment of the present invention employ a neural network to perform pattern recognition on the spectra of thermal luminescence collected by the sensor device. The neural network employed acts as a filter, i.e., it is trained to recognize spectral patterns of any-of-N contaminants or their hydrolysis (water sample) or/photo-fragmented products in the sensor's processed spectra outputs.

Once the neural network filter of this embodiment has matched a specific spectral pattern of absorption bands in the middle infrared region optical bandwidth of the sensor, the associated contaminant is identified.

Those skilled in the practice of FT-IR spectroscopy typically search for a structure of a particular molecular species by interrogating specific absorption bands correlating vibrational modes of atom groups comprising the molecular compound. The precise location (energy or frequency) and strength (amplitude) of the fundamental bands, i.e., the collective vibrations of primary atom groups, is often referred to as the fingerprint spectrum of the compound.

Using the present invention, thermal luminescence difference-spectra given off by a liquid sample are measured during an irradiation interval associated with a peak heating rate (or a state of maximum thermal luminescence flux). From these difference-spectra measurements, the absorption bands of the solute and the molecular identification of the contaminants in the sample are correlated. This is the detection technique employed by the system and method of the present invention, i.e., to radiometrically detect the molecular fingerprint spectra of contaminants in solution or to expose the absorption band features of the contaminant or its solute products carried in the thermal luminescence flux released from the liquid sample. If the contaminant compound hydrolyzes or photo-fragments when subjected to the microwave energy, the spectral search in thermal luminescence is conducted for the contaminant's associated fragmented and/or hydrolyzed product molecules. If the contaminant is inert, the spectral search is done on the intact contaminant molecular spectrum.

The system and method according to the invention allow attainment of the following advantages:

to reduce complexity of liquid quality analysis systems and methods;

to remotely sense liquid quality in real-time; and to increase accuracy of identification of contaminants.

This leads to improvements in the responsiveness and maintainability of the systems themselves resulting in improved liquid quality analyses which, in turn, leads to improvements in the timeliness and appropriateness of detection and response to liquid contamination. Overall the level of liquid quality is enhanced by the improvements flowing from the current invention.

BRIEF DESCRIPTION OF THE DRAWINGS

These and other characteristics of the invention will be evident from the following description of preferred embodiments, given as a non-restrictive example with reference to the attached drawings wherein like elements are numbered identically:

FIG. 3b illustrates a superposition of the Fourier transformation, in the mid-IR region, of the interferograms of FIG. 3a.

DETAILED DESCRIPTION OF THE PREFERRED EMBODIMENTS

The present invention is a remote sensing system and method that externally irradiate chemical and/or biological materials (CBMs) in a liquid with infrared microwave light that is tuned to an energy strongly absorbed by the solution, i.e., an energy that causes liquid molecules to resonantly rotate and vibrate, emitting characteristic thermal luminescence which is transformed into input to a pattern matching process for contaminant identification. Using the system and method of the present invention, the real-time sampling, irradiation and detection of CBMs dissolved in a liquid sample is possible.

Figure 1A:
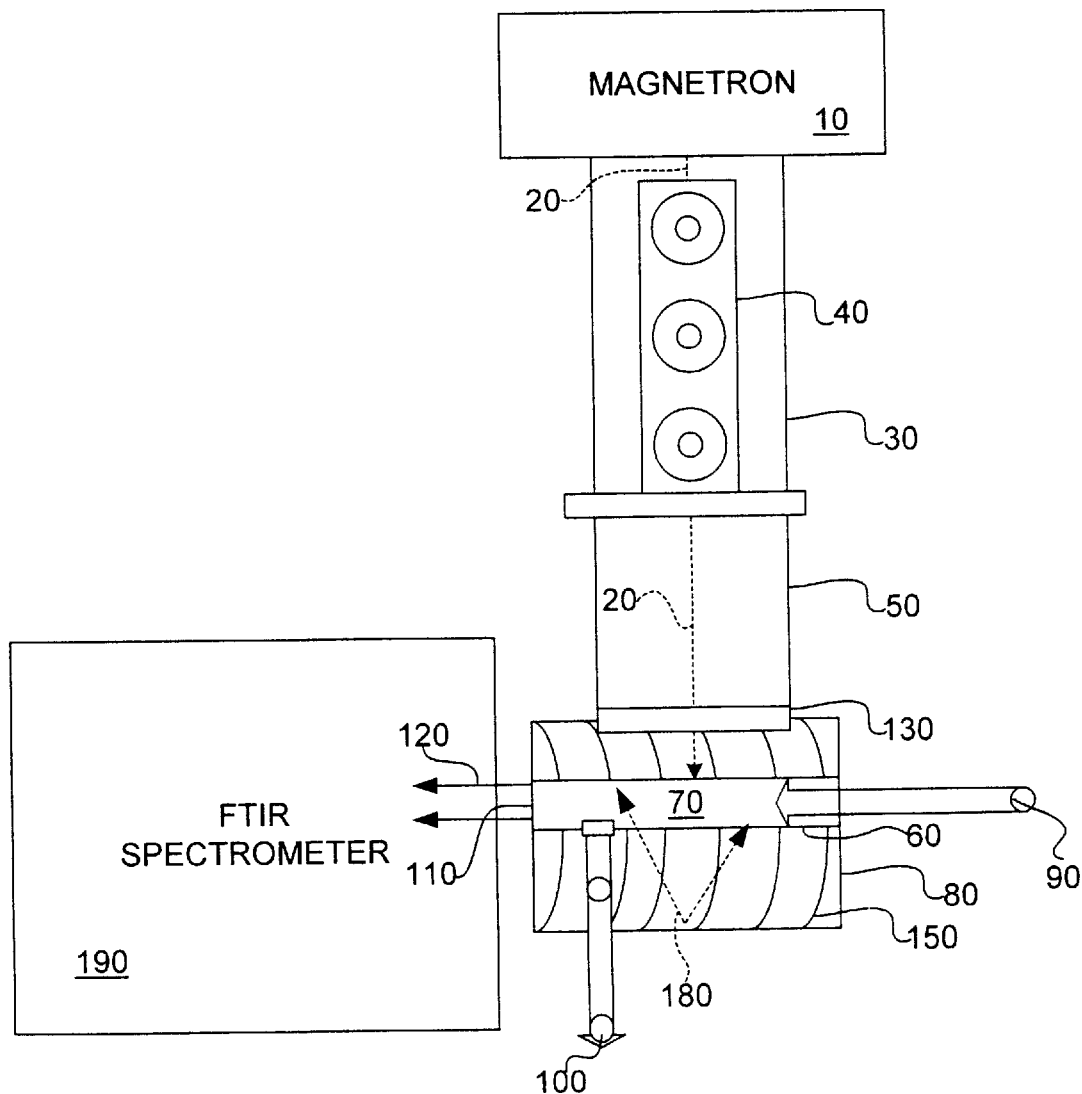
FIG. 1a is an illustration of the component parts of the present invention in a first embodiment which incorporates a cylindrical glass cell to hold a liquid sample.
Figure 1B:
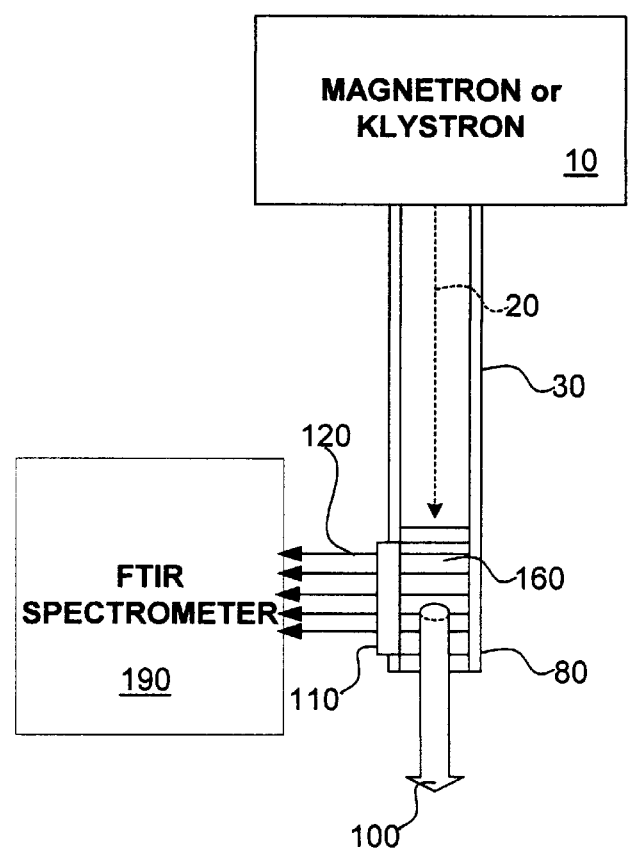
FIG. 1b is an illustration of the component parts of the present invention in a second embodiment which replaces the cylindrical glass cell with a disk.
Figure 2A:
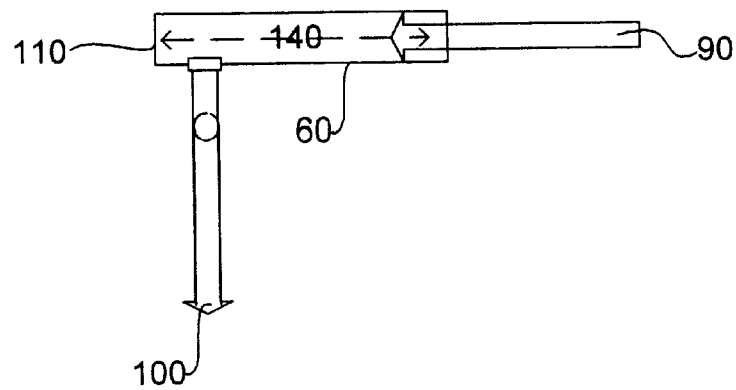
FIG. 2a is an illustration of a cylindrical sample cell of a first embodiment of the present invention.
Figure 2B:
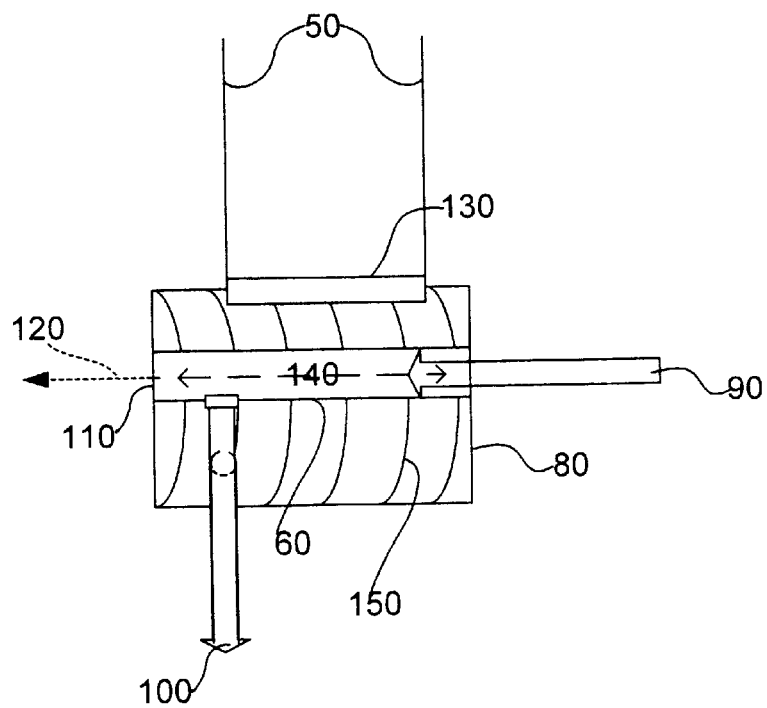
FIG. 2b is the metal chamber which holds the cylindrical glass cell of a first embodiment of the present invention.

One exemplary embodiment of the present invention is shown in FIG. 1a where a microwave beam source comprising a magnetron or klystron 10 emits an energetic beam 20, a length of microwave waveguide 30 for directing the microwave energy from the magnetron to a three-stub tuner 40 that regulates the microwave power generated by the magnetron 10, and another length of waveguide flange 50 couples the regulated microwave power to a cylindrical glass cell 60 holding the liquid sample 70 and encased by a metal microwave chamber 80 (see also FIG. 2b). In another exemplary embodiment of the current invention, illustrated in FIG. 1b, the tuner is omitted.

A liquid sample 70 is drawn into and held in a cylindrical glass cell 60 (see also FIG. 2a) with liquid intake port 90 and liquid output port 100 by pumping from a desired source, such as a pond, river or stream, into liquid intake port 90. The microwave beam 20 heats the liquid sample 70. One end of the cylindrical glass cell is fitted with a ZnSe window 110 that is coated so as to pass 96 percent or better of the infrared light 120 emanating from within the cylindrical glass cell 60 while it is irradiated with the incident microwave energy beam from its magnetron or klystron 10 source.

As illustrated in FIG. 2b a metal microwave chamber 80 is designed to encase the cylindrical glass cell 60, illustrated in FIG. 2a. In this encasement, a microwave input side 130 of the metal microwave chamber 80 couples to the end of magnetron waveguide flange 50. The axis 140 of the cylindrical glass cell 60 is parallel to and seated between the chamber's microwave input side 130 and the metal microwave chamber's opposite side 150 comprising a curved surface along the axis 140 of the cylindrical glass cell 60.

Figure 1C:
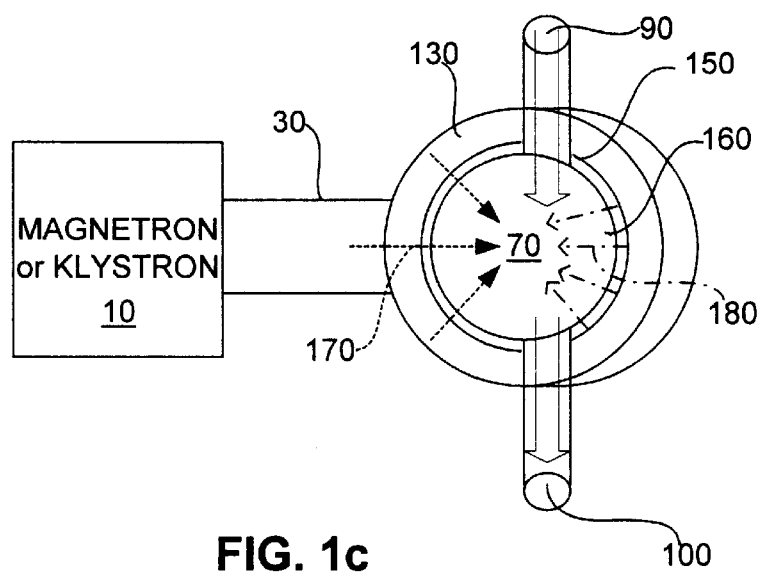
FIG. 1c is a side view of the disk of FIG. 1b.

In another exemplary embodiment, see FIG. 1b and FIG. 1c, the glass cell is configured as a disk 160 and the microwave input side 130 surrounds this disk 160 in a semicircle geometry to distribute the microwave energy to the liquid sample 70 in a radial pattern 170 with any non-absorbed microwaves reflected back in a radial pattern 180. In the disk configuration, radial heating further improves the system's and method's sensitivity of detection.

As illustrated in FIG. 1a, microwave energy that passes through the microwave input side 130 of the metal microwave chamber 80 is transparent to the cylindrical glass cell 60 or disk 160 material and near totally absorbed by the liquid sample within. Any microwave energy that happens to pass through the cylindrical glass cell 60 or disk 160 is reflected by the metal microwave chamber's curved surface 150 and reflected back 180 into the fluid contained in the cylindrical glass cell 60 or disk 160. Preferably, this curved surface 150 comprises a concave surface. In this manner, all of the incident microwave radiation is absorbed by the liquid sample 70 and converted into infrared radiance (thermal luminescence).

As shown in FIG. 1a and FIG. 1b, this infrared radiance passes through the ZnSe window 110 at the exitance end of the cylindrical glass cell or disk and is subsequently directed to a Fourier Transform Infrared (FT-IR) spectrometer 190 for detection and spectral processing of the thermal luminescent light. In another embodiment of the present invention the spectrometer incorporates an interferometer based on photoelastic modulation technology for producing higher signal-to-noise ratios and thus higher sensitivity of detection.

For a water sample, an embodiment of the present invention generates thermal luminescence from the water-solute sample via absorbed 2.45 GHz microwave energy. This thermal luminescence carries the fingerprint spectra of the CBMs in the sample, all having unique absorption bands in the 700–1400 $cm^{-1}$ optical bandwidth of the Fourier Transform spectrometer instrument. The spectra are measured by the spectrometer as the sample heats at maximum rate, i.e., as the thermal gradient between water and solute peaks. This region of maximum thermal gradient is termed the thermal detection window of opportunity.

In this embodiment of the present invention, a difference spectrum is calculated from contiguous spectra sets measured within this thermal detection window of opportunity. The difference spectrum is subsequently checked for parity (the absorption bands can be positive- or negative-going), baseline corrected, filtered, and auto-scaled for pattern recognition, and checked for absorption bands of CBMs through their photo-fragmented and/or hydrolysis product spectra. Finally, the difference-spectra are compared with known spectral data of CBMs using a neural network. A description of this technique is provided in U.S. Pat. No. 5,631,469 and U.S. Pat. application Ser. No. 09/546,742 both of which are hereby incorporated by reference herein.

In FIG. 3 the results of data collection and operation of the system are illustrated for a water sample, i.e., for the TLWM embodiment of the present invention. The microwave irradiation component can operate in continuous or pulsed-beam modes. When operated in the pulsed-beam mode, data is collected just before the downward pulse region of the pulsed beam, i.e., a period before the trailing edge of the microwave pulse. This corresponds to a heating interval where thermal luminescence flux exiting the cell is at a maximum, and the region where the thermal gradient between water and solute peaks at the absorption frequencies of the solute.

Figure 3A:
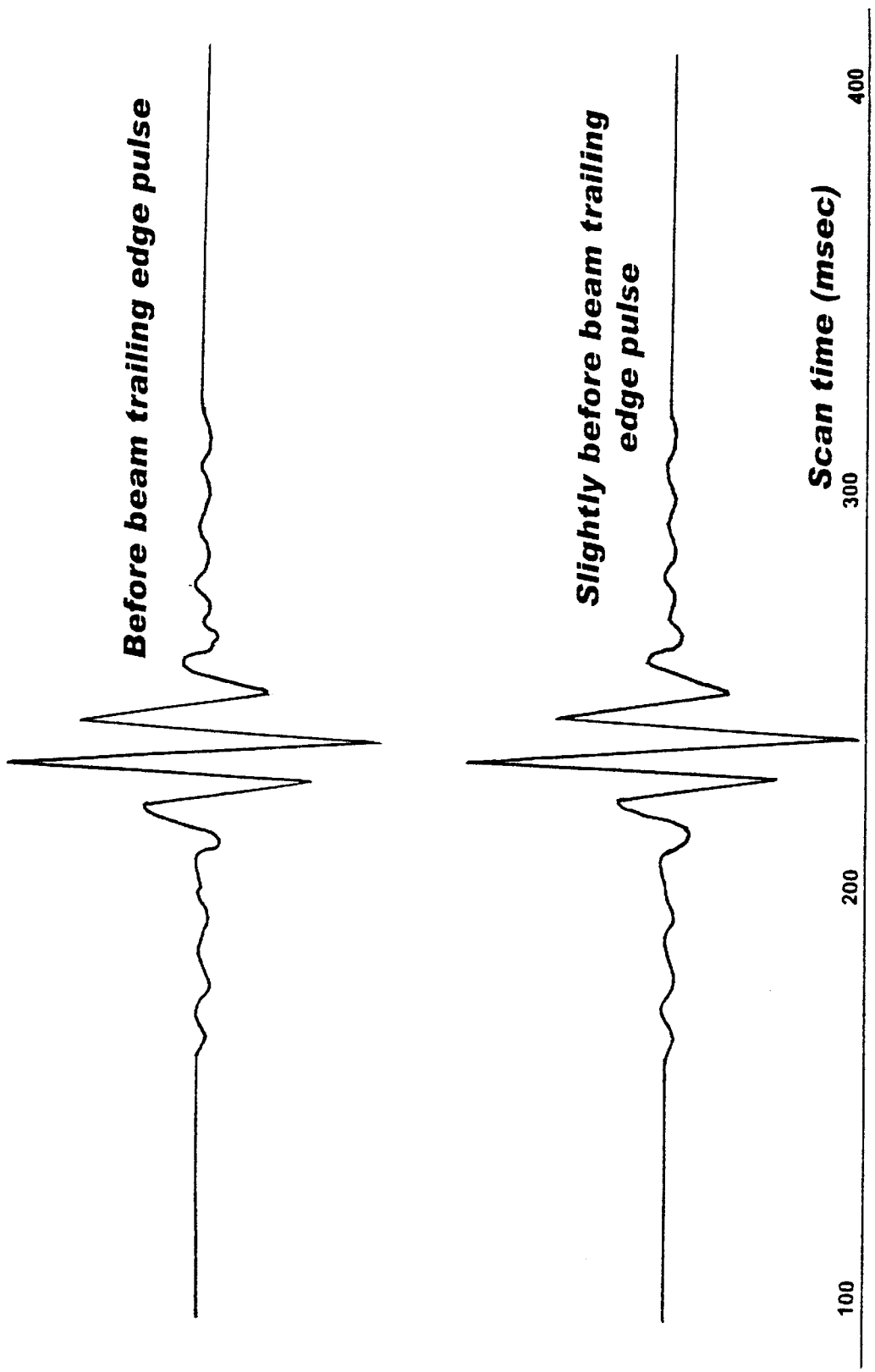
FIG. 3a shows the co-added, contiguous, raw interferogram data sets just prior to and before the trailing-edge pulse of microwave energy irradiating a sample of DMMP in water.
Figure 3C:
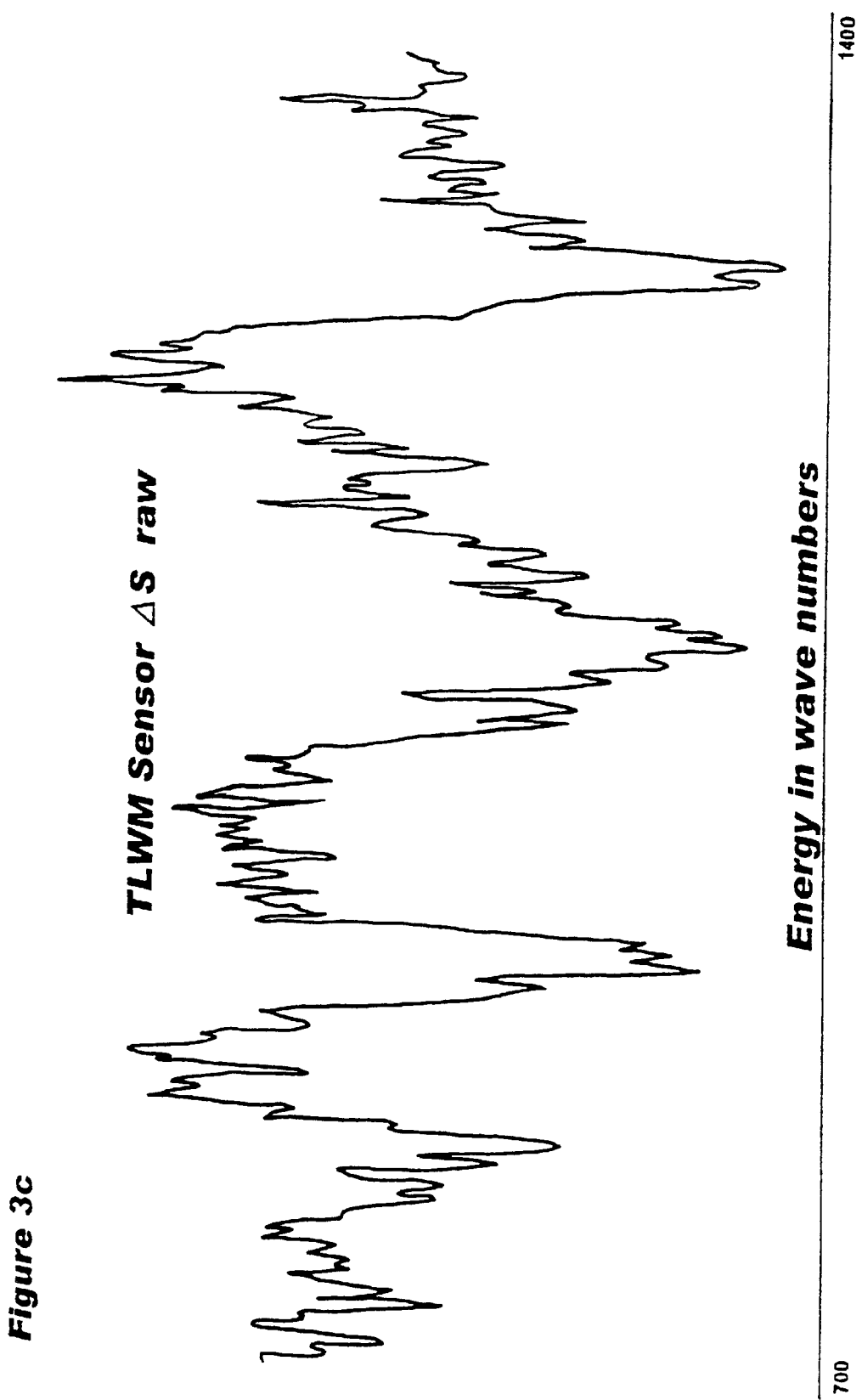
FIG. 3c shows the subtracted raw data of FIG. 3b.
Figure 3D:
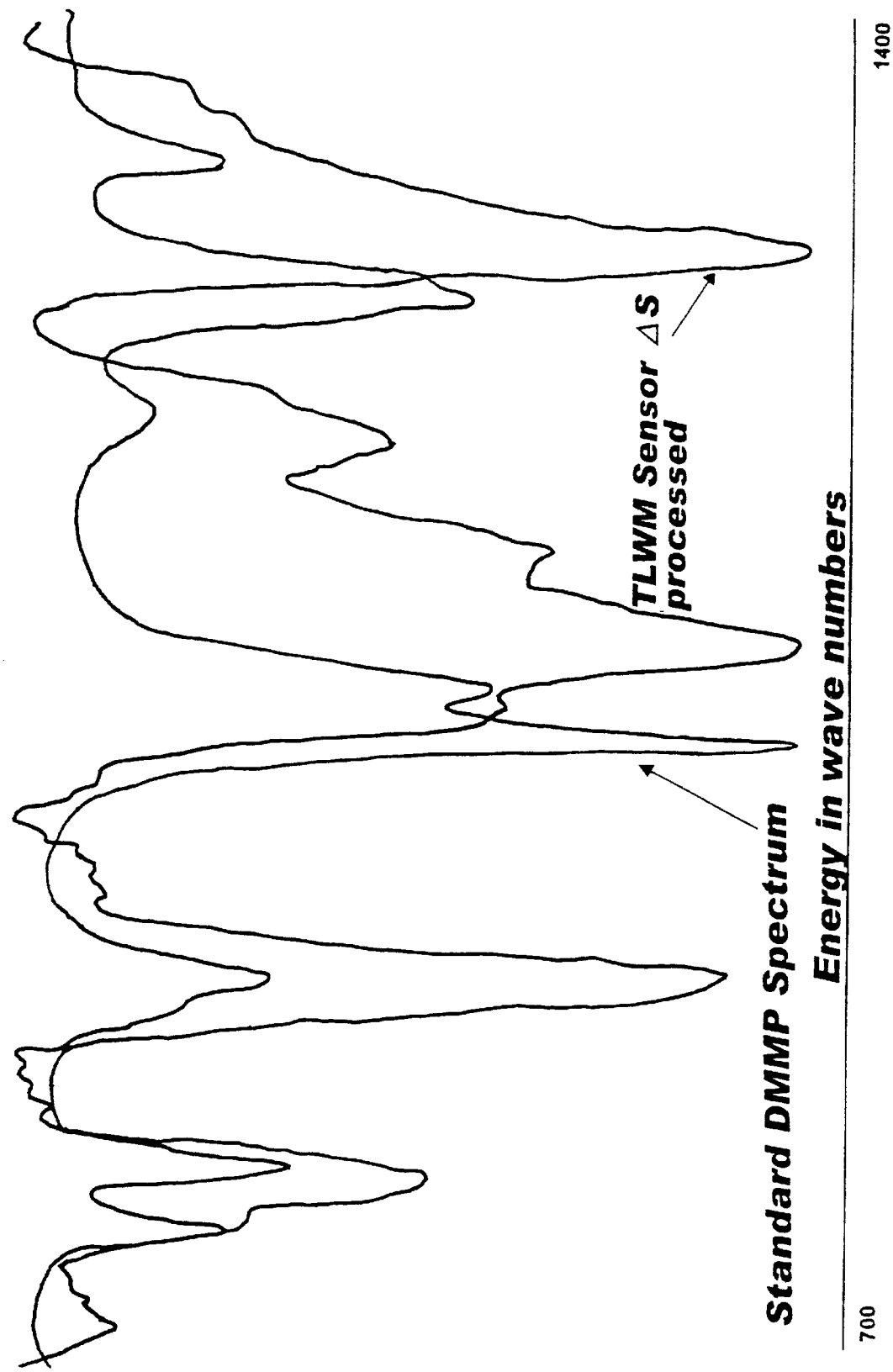
FIG. 3d compares the filtered and baseline corrected spectrum of FIG. 3c with the known spectrum of contaminant DMMP.

Illustrated in FIG. 3a are the co-added, contiguous, raw interferogram data sets taken by an exemplary embodiment of the TLWM embodiment just prior to and before the trailing-edge pulse of microwave energy that irradiates a sample of Dimethylmethylphosphonate (DMMP) in water. FIG. 3b illustrates a superposition of the Fourier transformation, in the 700–1400 $cm^{-1}$ middle infrared region, of the interferograms of FIG. 3a. Illustrated in FIG. 3c is the subtracted raw spectra of FIG. 3b. And, FIG. 3d compares the filtered and baseline corrected spectrum of FIG. 3c with the known spectrum of contaminant DMMP. By comparing the pure form DMMP spectrum to the subtracted and processed sensor spectra of FIG. 3d, one can deduce that the sensor has detected absorption band structure of DMMP's solute products, i.e., infrared energies activating resonant molecular vibration modes in the fragmented/hydrolyzed products of DMMP resulting from irradiation. When one or several differential-absorption bands from the sample are traced to the solute on a consistent basis, as illustrated in FIG. 3d, with sufficient signal-to-noise ratio, then these features are used to identify the parent contaminant material. In the TLWM embodiment of the present invention this pattern recognition is accomplished using a neural network which has been trained and validated to perform pattern recognition of specific contaminants.

Figure 4:
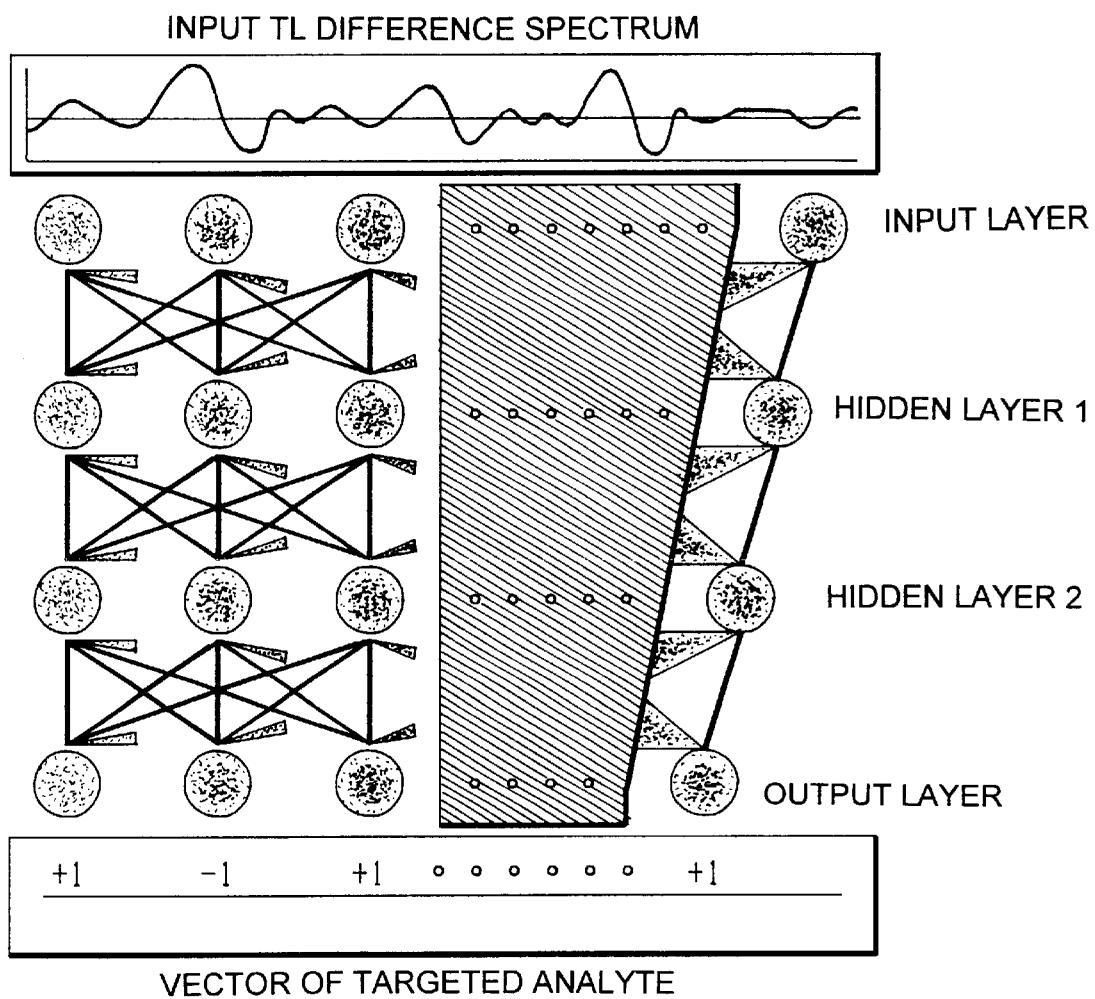
FIG. 4 represents neural network pattern recognition of the pre-processed data by an embodiment of the present invention.

FIG. 4 illustrates the architecture of such a neural network processor component for pattern recognition of specific contaminants. This illustrative neural network comprises an input layer of neuron or processing elements, two hidden layers, and an output layer. The input layer accepts the processed thermal luminescence difference-spectra measurement by an embodiment's sensor and the output layer represents n-components of a vector that uniquely identifies each contaminant. Feature space of the neural network is the known spectra of possible contaminants' solute products in a liquid, e.g., water solution, and under microwave irradiation. These feature spectra are used to train the neural network, providing partitioned domains from which to map the embodiment's incoming sensor-processed difference-spectral data into presence or absence of a specific CBM. The present invention provides a one-to-one mapping from a field of solute spectra onto their respective CBM targets. By placing processed thermal luminescence difference-spectra for known, expected contaminants into the neural network's feature space, the architecture illustrated in FIG. 4 supports neural network modeling, training, and testing.

Although the invention has been described by making detailed reference to certain specific embodiments, e.g., water and FR-IR spectrometer, such details are intended to be instructive rather than restrictive. It will be appreciated by those skilled in the art that many variations may be made in both structure and mode of operation without departing from the spirit and scope of this invention as disclosed in the teachings herein.

We claim:

1. A system for sensing and identifying chemical and biological contaminants in a liquid source, comprising:

a sample cell for containing a sample of the liquid source;

a metal chamber, said sample cell contained in said metal chamber;

a microwave irradiation source connected to said metal chamber and adapted to deliver microwave radiation to the sample contained in said sample cell to induce thermal luminescence of irradiated contaminants contained in the sample;

a spectral sensor aligned with said metal chamber to receive the thermal luminescence emitted from said sample, and for producing spectral data therefrom;

a spectral pattern recognizer trained to recognize specific spectral patterns in said spectral data for identifying said contaminants in the sample of the liquid source; and wherein said sample cell comprises a sample intake port for acquiring the liquid sample; a sample exit port for discharging the liquid sample; at least one wall for admitting the microwave radiation; and a thermal luminescence exitance window for delivering said luminescence to said spectral sensor.

2. The system of claim 1, wherein said sample cell comprises glass.

3. The system of claim 1, wherein said thermal luminescence exitance window comprises an infrared ZnSe window designed to index-match the water-ZnSe and ZnSe-air interfaces for maximum transmission of thermal luminescence exiting said sample cell; and wherein said irradiation source is tuned to an energy of 2.45 GHz.

4. The system of claim 1, wherein said intake port is attached to a first pump for acquiring the sample remotely from said liquid source, and said exit port is attached to a second pump means for discharging the sample.

5. The system of claim 4, wherein said first pump is adapted to regularly acquire the sample from the liquid source in real time, and said second pump is adapted to regularly discharge the sample after irradiation of said sample and before said first pumping means acquires another sample.

6. The system of claim 1, wherein said metal chamber further comprises:

an irradiation input port connected to said microwave irradiation source for transmitting said microwave radiation into said metal chamber to irradiate the sample contained in said sample cell contained therein;

a thermal luminescence output port for transmitting said thermal luminescence to said spectral sensor; and a reflective surface provided inside said metal chamber opposite said irradiation input port, for focusing non-absorbed radiation back into said sample cell.

7. The system of claim 6, wherein said reflective surface is concave.

8. The system of claim 1, wherein said spectral sensor comprises a Fourier Transform Infrared spectrometer having an interferometer and aligned with said metal container for spectral processing of said thermal luminescence to produce pre-processed spectral data.

9. The system of claim 8, wherein said interferometer is a Michelson interferometer.

10. The system of claim 8, wherein said interferometer is based on photoelastic modulation technology.

11. The system of claim 1, wherein said microwave irradiation source is a magnetron.

12. The system of claim 1, wherein said microwave irradiation source is a klystron.

13. The system of claim 1, wherein said spectral pattern recognizer is a neural network trained to recognize difference spectra of specific solute products of said irradiated contaminants.

14. The system of claim 13, wherein said spectral pattern recognizer employs pre-processed difference-spectra produced by said spectral sensor.

15. The system of claim 1, wherein said metal chamber further comprises a microwave irradiation window having a longitudinal axis and adapted to being connected to said microwave irradiation source, and said sample cell is a glass cylinder having a longitudinal axis parallel to said longitudinal axis of said microwave irradiation window.

16. The system of claim 1, wherein said sample cell is a glass disk, and said microwave irradiation source further comprises an input port having said input port surround said glass disk in a semi-circle geometry such that said microwave radiation is distributed to the sample in a radial pattern.

17. The system of claim 1, wherein said microwave irradiation source is adapted to deliver pulsed microwave radiation.

18. The system of claim 1, wherein said microwave irradiation source is adapted to deliver continuous microwave radiation.

19. The system of claim 1, wherein said metal chamber is sealed to prevent the loss of microwave radiation to the atmosphere.

20. An apparatus for sensing and identifying chemical and biological contaminants in a liquid source, comprising:

a glass sample cell for containing a sample of the liquid source, said cell having an intake port for receiving the sample, an exit port for discharging the sample, at least one wall for admitting microwave radiation, and a thermal luminescence exitance window;

a microwave source for irradiating with microwave radiation said contaminants in the liquid sample to produce thermal luminescence;

a sealed metal chamber adapted to contain said glass sample cell, said sealed metal chamber having an irradiation input port Connected to said microwave source for transmitting said microwave radiation into said sealed metal chamber and irradiating the sample contained in said glass sample cell to produce thermal luminescence, and having a reflective surface provided inside said sealed metal chamber opposite said irradiation input port for reflecting non-absorbed radiation back into said glass sample cell;

a spectral analyzer aligned with said thermal luminescence exitance window and adapted to receive said thermal luminescence and produce spectral data therefrom in real-time;

a pattern recognizer trained for identifying specific contaminants from said spectral data in real-time;

a first pump connected to said intake port and adapted for regularly acquiring the sample from the liquid source in real-time; and a second pump connected to said exit port and adapted for regularly emptying the sample from said glass sample cell subsequent to analysis of the sample and before said first pump acquires another sample.

21. An apparatus for sensing and identifying chemical and biological contaminants in a water source, comprising:

a glass sample cell for containing a sample of the water source, said cell having an intake port for regularly receiving the sample, an exit port for regularly discharging the sample, and a ZnSe thermal exitance window designed to index-match the water-ZnSe and ZnSe-air interfaces for maximum transmission of thermal luminescence exiting said glass sample cell;

a microwave radiation source tuned to about 2.45 GHz for irradiating said contaminants in the water sample with microwave radiation to produce thermal luminescence;

a scaled metal chamber adapted to contain said glass sample cell, said chamber having an irradiation input port connected to said microwave radiation source for transmitting said microwave radiation into said sealed metal chamber to irradiate the sample contained in said glass sample cell, and having a reflective surface provided inside said sealed metal container opposite said irradiation input port for focusing non-absorbed radiation back into said glass sample cell;

a spectral analyzer aligned with said thermal luminescence exitance window adapted to receive said thermal luminescence and produce spectral data therefrom in real-time;

a pattern recognizer trained for identifying specific contaminants from said spectral data in real-time;

a first pump connected to said intake port adapted for regularly acquiring the sample from the water source in real-time; and a second pump connected to said exit port adapted for regularly emptying the sample from said glass sample cell subsequent to spectral analysis and pattern recognition and before said first pump acquires another sample.

* * * * *